United States Patent [19]

Goure et al.

[11] Patent Number: 4,785,129

[45] Date of Patent: Nov. 15, 1988

[54] METHYL 4,4,4-TRIFLUORO-3-OXO-BUTANETHIOATE

[75] Inventors: William F. Goure, Maryland Heights; Len F. Lee, St. Charles, both of Mo.

[73] Assignee: Monsanto Company, St. Louis, Mo.

[21] Appl. No.: 156,115

[22] Filed: Feb. 16, 1988

[51] Int. Cl.[4] .......................................... C07C 153/09
[52] U.S. Cl. .................................................. 558/253
[58] Field of Search ........................................ 558/253

[56] References Cited

U.S. PATENT DOCUMENTS 4,491,547 1/1985 Tsuji et al. ........................ 558/253

Primary Examiner—Alan L. Rotman
Assistant Examiner—Robert C. Whittenbaugh
Attorney, Agent, or Firm—James C. Bolding

[57] ABSTRACT

Disclosed herein is 4,4,4-trifluoro-3-oxo-butanethioate, a useful starting material in the preparation of pyridinedicarboxylate herbicides.

1 Claim, No Drawings

METHYL 4,4,4-TRIFLUORO-3-OXO-BUTANETHIOATE

This invention deals with methyl 4,4,4-trifluoro-3-oxo-butanethioate as a novel compound useful as a reactant in the preparation of pyridine carbothioate amd carbodithioate herbicides such as those of U. S. Pat. Nos. 4,692,184; 4,698,093; and 4,655,816.

Methyl and ethyl esters of 4,4,4-trifluoro -3-oxo-butanoic acid are known compounds and are commercially available. The ester of this acid with methanethiol has not, however, been heretofore known, nor has a utility for it been known.

DESCRIPTION OF THE INVENTION

As was stated above, the compound of this invention is methyl 4,4,4-trifluoro-3-oxo-butanethioate, also known as thiomethyl trifluoroacetoacetate (TMTFAA).

This compound is prepared by the reaction of trifluoroacetyl chloride with ketene to yield 4,4,4-trifluoro-3-oxo-butyryl chloride, followed by thioesterification with methanethiol to yield the compound of this invention. Although the reaction proceeds in two steps, the intermediate acid chloride is highly reactive and is not isolated. The reaction is preferably carried out in solution, and the solvent may be, for example, dichloromethane, toluene, dichloroethane, or the like. Preparation of this compound is shown in the following example.

EXAMPLE

Trifluoroacetyl chloride, methyl mercaptan (methanethiol), acetic anhydride and toluene solvent were used as purchased without further purification.

Preparation of Ketene

Ketene was prepared by the pyrolysis of acetic anhydride following the general procedure of Fisher and MacLean; see F. Maclean, *J.O.C.*, 18, 1055 (1953). Acetic anhydride was pumped via gear pump to an oil jacketed Pyrex vaporizer maintained at 160° C. The vapor was then passed through a quartz tube packed with ¼ inch ceramic saddles and directly into a coiled condenser maintained at a jacket temperature of −18 to −22° C. The tube was heated by a furnace and was maintained at 510°–520° C. The vapor was then passed through a set of cyclone separators which rapidly separated the ketene stream from the acetic anhydride. The cyclones were maintained at 15° C.

Preparation of TMTFAA

The apparatus utilized was a round-bottomed flask equipped with magnetic stirrer, thermometer, dry ice condenser, and dry ice cooled addition tube. The glassware was oven dried, assembled and allowed to cool under a continuous flow of dry nitrogen. Toluene as a solvent was added first and the overhead condenser (dry ice-acetone) and cooling bath (dry ice-CCl4) were charged. Trifluoroacetyl chloride was then charged (40.0 g, 0.3018 mol) by passing it through the overhead condenser and liquifying it into the reactor. When the addition of trifluoroacetyl chloride was complete the ketene addition was started. The ketene was passed through the same condenser and liquified into the trifluoroacetyl chloride. During the addition of ketene the reaction was exothermic. The reactor temperature was maintained at −10° to −12° C. After the ketene addition was complete the reaction was stirred at or below −10° C. for 30 min. The reaction was then quenched with 1.5–2.0 equivalents of methyl mercaptan which was added by passing it through the overhead condenser. The reaction was maintained below −10° C. by controlling the addition rate of methyl mercaptan. After the methyl mercaptan addition was complete the reaction was allowed to warm to room temperature (1.0–1.5 hr). The reaction mixture was then heated to 90° C. for approximately 20 min in order to degas the mixture. The reaction mixture was also distilled to yield high quality compound of this invention, b.p. 78°–80° C. @ 73 torr. The structure was confirmed by $^1$H and $^{19}$F NMR and by gas chromatograph/mass spectrometer analysis.

As was stated above, this compound is useful as a starting material in the preparation of pyridine herbicides. More particularly, the pyridine carbodithioate herbicides of U. S. Pat. No. 4,692,184 may be prepared by reaction of this compound with an aldehyde to form a pyran, conversion of the pyran to a dihydroxypiperidine by treatment with ammonia, dehydration to form a dihydropyridine, etc. The compound of this invention is simply substituted for the corresponding 4,4,4-trifluor-3-oxo-butanoate ester used in that patent, the disclosure of which is incorporated herein by reference.

We claim:

1. Methyl 4,4,4-trifluoro-3-oxo-butanethioate.

* * * * *